(12) United States Patent
Altman et al.

(10) Patent No.: US 11,443,425 B2
(45) Date of Patent: Sep. 13, 2022

(54) FAST ANATOMICAL MAPPING (FAM) RECONSTRUCTION USING SURFACE UPDATE RESTRICTIONS

(71) Applicant: BIOSENSE WEBSTER (ISRAEL) LTD., Yokneam (IL)

(72) Inventors: Sigal Altman, Ramat Hashofet (IL); Fady Massarwa, Baka Al Gharbiyya (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 261 days.

(21) Appl. No.: 16/852,803

(22) Filed: Apr. 20, 2020

(65) Prior Publication Data

US 2021/0327053 A1 Oct. 21, 2021

(51) Int. Cl.
*A61B 5/339* (2021.01)
*G06T 7/00* (2017.01)
*A61B 5/316* (2021.01)
*A61B 5/287* (2021.01)

(52) U.S. Cl.
CPC ............ *G06T 7/0012* (2013.01); *A61B 5/316* (2021.01); *A61B 5/339* (2021.01); *A61B 5/287* (2021.01); *G06T 2200/24* (2013.01); *G06T 2207/30048* (2013.01); *G06T 2207/30101* (2013.01)

(58) Field of Classification Search
CPC .............. G06T 7/0012; G06T 2200/24; G06T 2207/30048; G06T 2207/30101; G06T 2210/41; G06T 2210/56; G06T 2219/2021; G06T 19/20; A61B 5/316; A61B 5/339; A61B 5/287; A61B 18/12; A61B 18/1492; A61B 2018/00351; A61B 2018/00541; A61B 2018/00577; A61B 2018/00839; G16H 30/40
See application file for complete search history.

(56) References Cited

U.S. PATENT DOCUMENTS

| | | | |
|---|---|---|---|
| 8,456,182 | B2 | 6/2013 | Bar-Tal |
| 2003/0236466 | A1 | 12/2003 | Tarjan |
| 2015/0018698 | A1 | 1/2015 | Safran |
| 2017/0325891 | A1 | 11/2017 | Harlev |
| 2017/0340227 | A1 | 11/2017 | Altmann |
| 2018/0190009 | A1 | 7/2018 | Cohen |
| 2020/0051247 | A1 | 2/2020 | Groth |

FOREIGN PATENT DOCUMENTS

WO  WO-2019051464 A1 * 3/2019  ............. A61B 34/20

OTHER PUBLICATIONS

European Search Report for corresponding EPA No. 21169093.8 dated Sep. 16, 2021.
CARTO 3 System—Instructions for Use—UG-5400-006H (05A), Mar. 10, 2019, pp. 1-291.

* cited by examiner

*Primary Examiner* — Siamak Harandi

(57) ABSTRACT

A method includes presenting, on a display, an electroanatomical (EA) map of a surface of a cavity of an organ. Input is received from a user, and, in response to the user input, a region of the EA map is locked to subsequent updates.

12 Claims, 2 Drawing Sheets

FAST ANATOMICAL MAPPING (FAM) RECONSTRUCTION USING SURFACE UPDATE RESTRICTIONS

FIELD OF THE INVENTION

The present invention relates generally to electroanatomical (EA) mapping, and particularly to editing of cardiac EA maps.

BACKGROUND OF THE INVENTION

Software-based editing tools for assisting the analysis of an electroanatomically mapped organ were previously proposed in the patent literature. For example, U.S. Patent Application Publication 2017/0325891 describes methods directed to generating three-dimensional surface representations of an anatomic structure such as a heart cavity. More specifically, a three-dimensional surface representation of the anatomic structure is constrained relative to one or more anchor portions corresponding to received input regarding the location of anatomic features of the anatomic structure. The resulting three-dimensional surface representation includes salient features of the anatomic structure and, therefore, can be useful as a visualization tool during any of various different medical procedures, including, for example, cardiac ablation.

SUMMARY OF THE INVENTION

An embodiment of the present invention that is described hereinafter provides a method including presenting, on a display, an electroanatomical (EA) map of a surface of a cavity of an organ. Input is received from a user, and, in response to the user input, a region of the EA map is locked to subsequent updates.

In some embodiments, locking the region includes preventing subsequent manual editing of the EA map.

In some embodiments, locking the region includes ignoring subsequently acquired data points belonging to the region.

In other embodiments, locking the region includes preventing subsequent updates in prespecified proximity of an anatomical feature in the EA map.

In an embodiment, the EA map includes an EA map of a left atrium, and wherein the anatomical feature is a pulmonary vein.

In another embodiment, locking the region is performed in response to identifying that data points in the region were obtained by a probe while applying excessive force to the surface.

In some embodiments, the method further includes manually editing unlocked regions of the EA map to remove irrelevant data points therein.

In some embodiments, the method further includes unlocking the locked region. The unlocked region of the EA map is manually edited to remove irrelevant data points therein, and the manually edited region is re-locked.

There is additionally provided, in accordance with another embodiment of the present invention, a system including a display and a processor. The display is configured to present an electroanatomical (EA) map of a surface of a cavity of an organ. The processor is configured to receive input from a user, and, in response to the user input, to lock a region of the EA map to subsequent updates.

BRIEF DESCRIPTION OF THE DRAWINGS

The present invention will be more fully understood from the following detailed description of the embodiments thereof, taken together with the drawings in which.

Detailed Description of Embodiments

Overview

Figure 1:
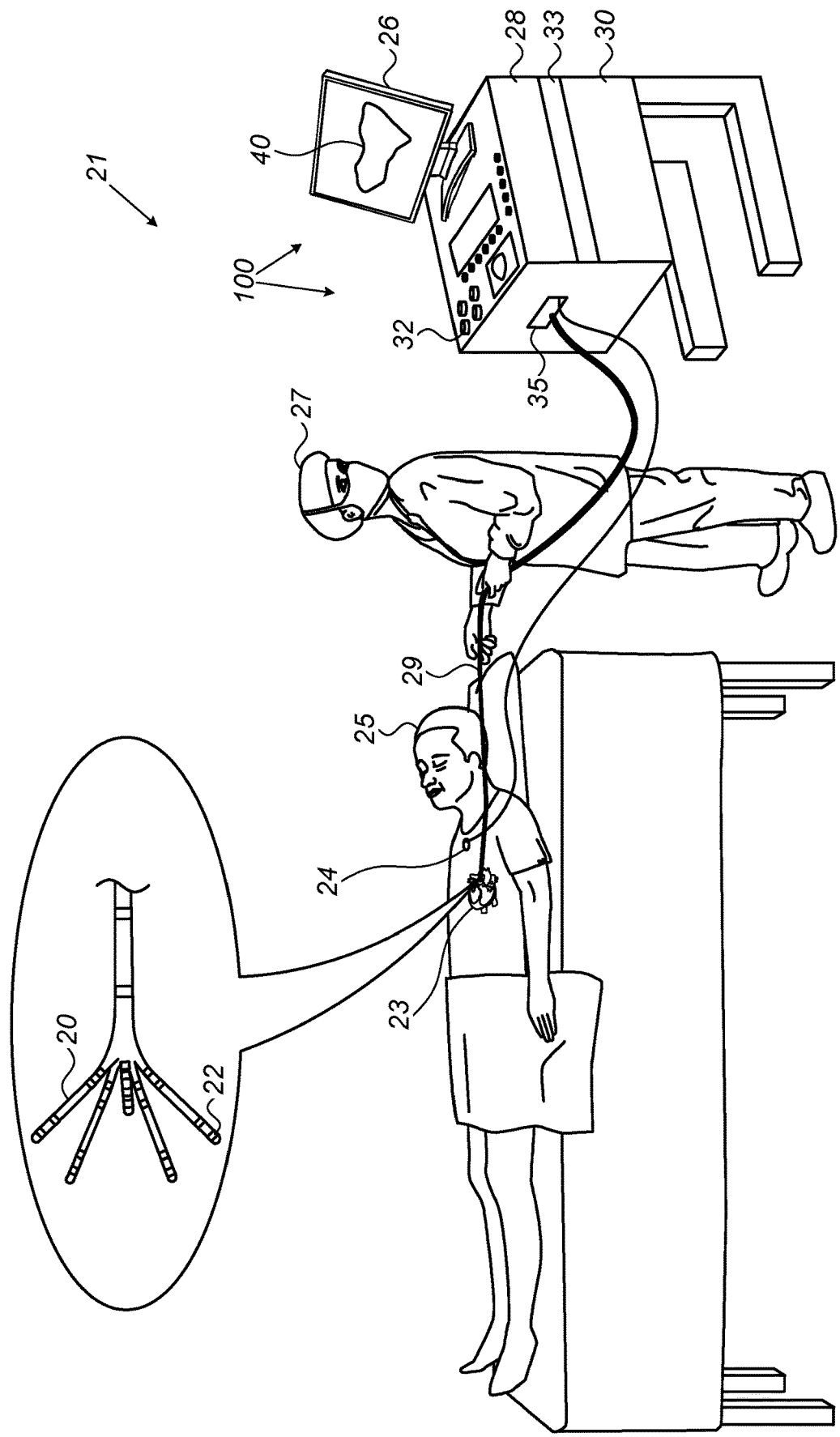
FIG. 1 is a schematic, pictorial illustration of a system for electroanatomical (EA) mapping, in accordance with an exemplary embodiment of the present invention.

An interior of an organ of a patient, such as a cardiac cavity, can be mapped using a mapping catheter (e.g., electroanatomically mapped) having one or more suitable sensors fitted at its distal end for mapping within the organ. Using location signals generated by the various sensors, a processor may calculate the sensor locations within the organ (e.g., the cardiac cavity). Using the calculated locations, the processor may further derive an anatomical map of the cavity surface.

For example, in a fast-anatomical mapping (FAM) of a heart chamber, point positions on an inner surface of the cavity are drawn using acquired electroanatomical (EA) data. However, undesired catheter positions may also be acquired and automatically added to the FAM-constructed cavity surface during FAM reconstruction. Examples of such undesired data points include cavity wall positions distorted by being pushed outwards by the catheter, wrong wall positions due to respiration-induced movement, positions measured erroneously in the interior of the cavity instead of on the surface, and irrelevant catheter positions, e.g., outside a mapping area of interest.

The accumulation of such undesired positions affect the accuracy of the reconstructed EA map. To address these inaccuracies, during or after acquisition, a physician, or a specialist helping the physician, may manually edit the surface generated from the acquired points to correct for the errors. This manual editing typically involves erasing data points and/or removing ("shaving") entire portions from the computed surface. However, this manual editing is a time-consuming process.

Exemplary embodiments of the present invention that are described herein reduce the amount of manual editing needed by "locking" regions (e.g., areas) of a surface of an EA map presented to a user, wherein those areas are not to be further edited (e.g., to prevent automatically made updates and/or manual edits of the region of the EA map).

In the disclosed exemplary embodiments, a user interface is provided that enables the user to provide an input, such as to command the mapping system to lock a region of the EA map shown on a display to subsequent updates. For example, in response to the user input, a processor of the system ignores subsequently acquired data points belonging to the region. In some exemplary embodiments, FAM-generated surface areas of the map that are deemed good enough are "locked" by the user so as not to be further updated automatically by the mapping application, thus preventing accumulation of new errors in these areas.

Examples of locked regions include:
- A surface portion that has already been manually edited. Further automatic acquisitions in that region are ignored, though the region may still be manually edited.
- Acquisitions for which a measured catheter contact force is deemed above a predefined threshold (indicating that the catheter is pushing wall tissue locally to a distorted position). Acquired points are ignored and are not used to construct the surface.
- Certain areas on the map that, after an initial FAM mapping, are deemed sufficiently representative of the anatomy. An example of such an area is around an ostium of pulmonary veins in an EA map of the left atrium of the heart.

In some exemplary embodiments, the disclosed user interface includes controls configured to undo existing update restrictions. For example, a special editing mode is activated (e.g., as a keyboard button) to enable data point updates even in locked areas, for example, in the most recent locked area. An editing mode may also be provided as a new acquisition mode in the FAM tool user interface. Another control (e.g., a computer mouse) can be activated, as another example, to manually select "locked" areas on the surface and disable ("unlock") its update restrictions. A further control knob, such as another keyboard button, may be used to toggle the entire update restriction mode on or off.

The disclosed FAM surface update restriction techniques may assist the physician to prepare an EA map, and thus ease, expedite and improve the quality of complicated diagnostic tasks performed during diagnostic catheterizations, which rely on an accurate EA map generated during the procedures. Another advantage of the disclosed FAM surface update restriction techniques is reducing the editing (e.g., shaving) time of portions of the map or the acquired data (e.g., volume) that is used to build the map.

System Description

FIG. 1 is a schematic, pictorial illustration of a system 21 for electroanatomical (EA) mapping, in accordance with an exemplary embodiment of the present invention. FIG. 1 depicts a physician 27 using a Pentaray® EA mapping catheter 29 to perform an EA mapping of a heart 23 of a patient 25. Catheter 29 comprises, at its distal end, one or more arms 20, which may be mechanically flexible, each of which is coupled with one or more electrodes 22. During the mapping procedure, electrodes 22 acquire and/or inject unipolar and/or bipolar signals from and/or to the tissue of heart 23.

A processor 28 in a console 30 receives these signals via an electrical interface 35, and uses information contained in these signals to construct an EA map 40 that processor 28 stores in a memory 33. During and/or following the procedure, processor 28 may display EA map 40 on a display 26. User controls 32 of a user interface 100 enable physician 27 to communicate with processor 28 to lock portions of EA map 40 to prevent further updating, as described above. Controls 32 may include, for example, a trackball and control knobs, as well as a keyboard. Other elements of user interface 100 may include touch screen functionality of display 26.

During the procedure, a tracking system is used to track the respective locations of sensing-electrodes 22, such that each of the signals may be associated with the location at which the signal was acquired. For example, the Active Current Location (ACL) system, made by Biosense-Webster (Irvine, Calif.), which is described in U.S. Pat. No. 8,456,182, whose disclosure is incorporated herein by reference, may be used. In the ACL system, a processor estimates the respective locations of the electrodes based on impedances measured between each of the sensing electrodes 22, and a plurality of surface electrodes 24, that are coupled to the skin of patient 25. For example, three surface electrodes 24 may be coupled to the patient's chest, and another three surface electrodes may be coupled to the patient's back. For ease of illustration, only one surface electrode 24 is shown in FIG. 1. Electric currents are passed between electrodes 22 inside heart 23 of the patient 25 and surface electrodes 24. Processor 28 calculates an estimated location of all electrodes 22 within the patient's heart 23 based on the ratios between the resulting current amplitudes measured at surface electrodes 24 (or between the impedances implied by these amplitudes) and the known positions of electrodes 24 on the patient's body. The processor 28 may thus associate any given impedance signal received from electrodes 22 with the location at which the signal was acquired.

The example illustration shown in FIG. 1 is chosen purely for the sake of conceptual clarity. Other tracking methods can be used, such as those based on measuring voltage signals. Other types of sensing catheters, such as the Lasso® Catheter (produced by Biosense Webster) may equivalently be employed. Contact sensors may be fitted at the distal end of EA mapping catheter 29. As noted above, other types of electrodes, such as those used for ablation, may be utilized in a similar way and fitted to electrodes for acquiring the needed position data. Thus, an ablation electrode used for collecting position data is regarded, in this case, as a sensing electrode. In an optional exemplary embodiment, processor 28 is further configured to indicate the quality of physical contact between each of the electrodes 22 and an inner surface of the cardiac chamber during measurement.

Processor 28 typically comprises a general-purpose computer with software programmed to carry out the functions described herein. In particular, processor 28 runs a dedicated algorithm as disclosed herein, including in FIG. 3, which enables processor 28 to perform the disclosed steps, as further described below. The software may be downloaded to the computer in electronic form, over a network, for example, or it may, alternatively or additionally, be provided and/or stored on non-transitory tangible media, such as magnetic, optical, or electronic memory.

FAM Reconstruction Using Surface Update Restrictions

Figure 2:
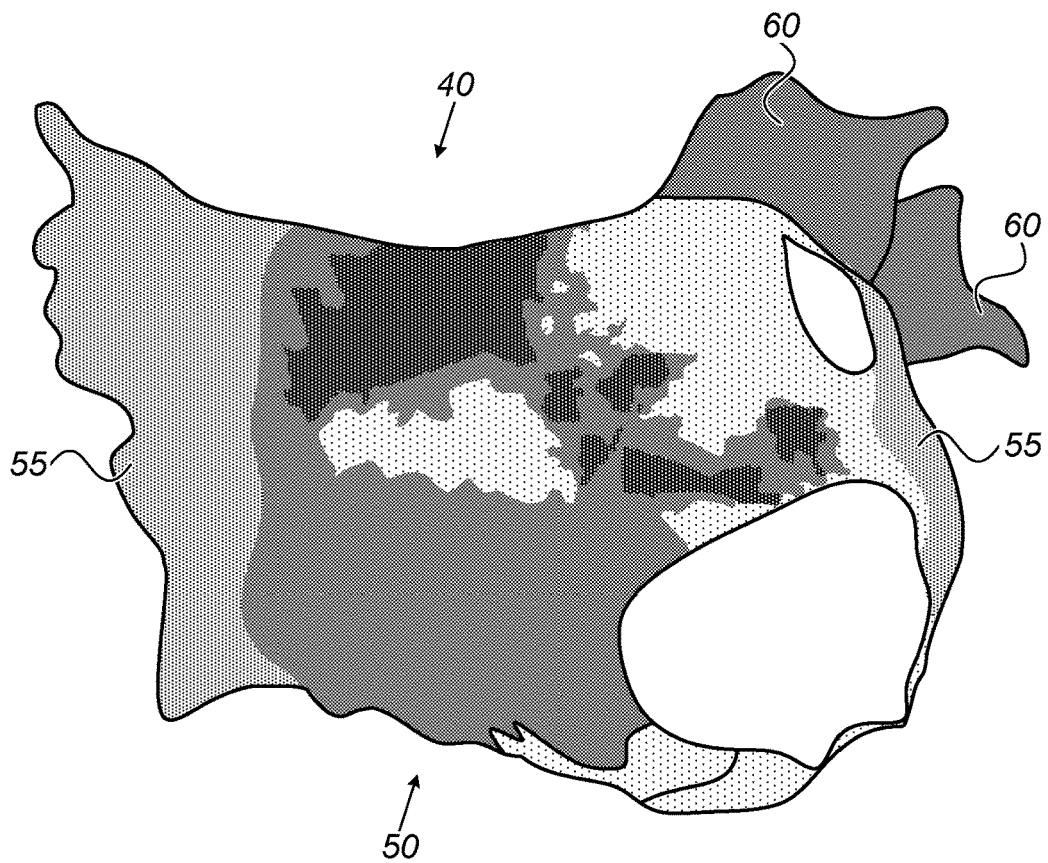
FIG. 2 is a schematic, pictorial illustration of a reconstructed electroanatomical (EA) map of a left atrium generated using surface update restrictions, in accordance with an exemplary embodiment of the present invention.

FIG. 2 is a schematic, pictorial illustration of a reconstructed electroanatomical (EA) map 40 of a left atrium generated using surface update restrictions, in accordance with an exemplary embodiment of the present invention. Map 40 comprises different areas, some of which, such as areas in a region 50, being open to automatic updating according to new data points acquired during the mapping procedure shown in FIG. 1. Areas 60, which are EA-mapped surfaces of ostia of pulmonary veins, are locked for further editing by the physician because areas 60 of EA map 40 are deemed sufficiently representative of the anatomy. Map 50 further comprises areas 55 which were locked after being previously manually edited.

As seen, areas with a different status (e.g., locked or actively updated) can be emphasized graphically, for example, with different shades or textures, so that the physician may readily follow the progress of the EA mapping.

FIG. 2 is brought purely for clarity of description. In other exemplary embodiments, for example, EA map 40 may include additional information, such as values of electrophysiological potentials and cardiac activation times.

Figure 3:
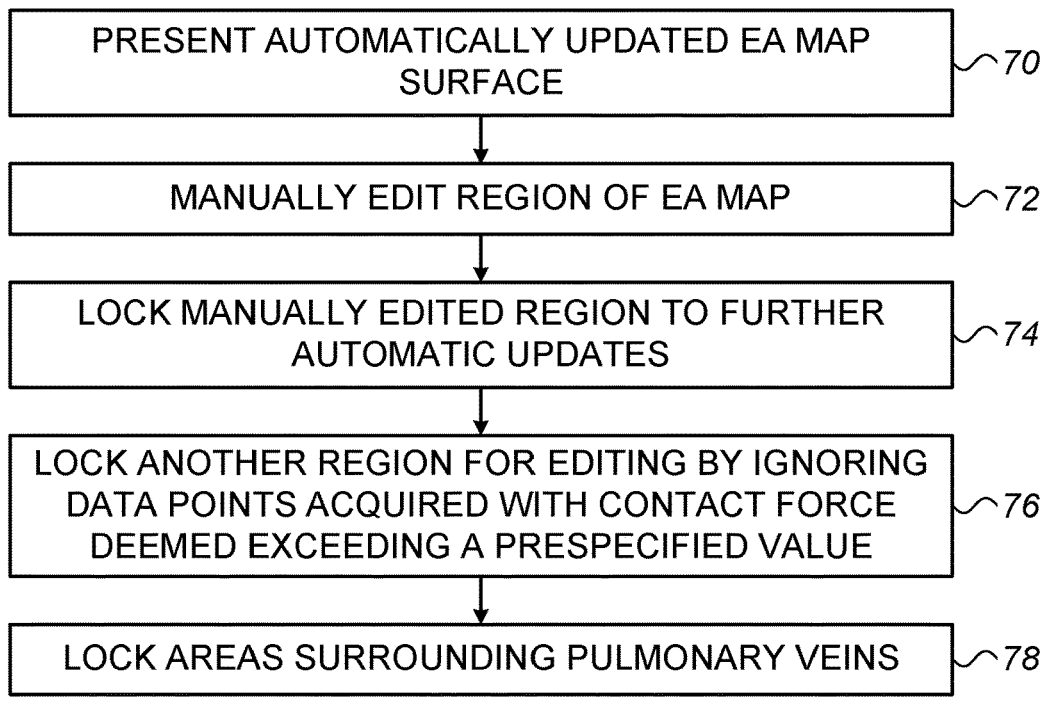
FIG. 3 is a flow chart that schematically describes a method for generating the reconstructed electroanatomical (EA) map of FIG. 2, in accordance with an exemplary embodiment of the present invention.

FIG. 3 is a flow chart that schematically describes a method for generating the reconstructed electroanatomical (EA) map 40 of FIG. 2 (i.e., using surface update restrictions), in accordance with an exemplary embodiment of the present invention. The algorithm, according to the presented embodiment, carries out a process that begins with processor 28 presenting to a user an EA map 40 that also undergoes automatic updates by processor 28 as the processor analyzes newly acquired data points and adds these to EA map 40 at step 70.

At a manual editing step 72, using user interface 100, physician 27 edits a region of map 40, for example by erasing erroneous data points that distort the presented anatomical shape. Next, at a locking step 74, physician 27 locks the edited area, such as area 55, to avoid it being updated with newly acquired erroneous data points. To lock the region, physician 27 uses control tools 32 of user interface 100 to select an area and change its status.

At an additional locking step 76, physician 27 turns to a map area being actively updated. In order to avoid extensive manual editing to erase distortive data points (such as taken in step 72), the physician locks the area to updates with data points that processor 28 determines were erroneous, since they were acquired while the catheter applied excessive contact force on wall tissue (e.g., a force above a prespecified value being applied to the surface of the cavity). Finally, at step 78, physician 27 locks editing in regions 60 in proximity of ostia of pulmonary veins, after deciding that additional data points in those areas are not important enough to justify a potential need to manually edit those regions of the EA map.

The example flow chart shown in FIG. 3 is chosen purely for the sake of conceptual clarity. In optional exemplary embodiments, various additional steps may be performed, for example to automatically register additional layers, such as of medical images.

Although the embodiments described herein mainly address cardiac applications, the methods and systems described herein can also be used in other applications, such as in anatomical mapping of cavities of other organs of the body. In general, the disclosed update restrictions techniques can be used in any application that utilizes a geometrical map reconstruction algorithm that is incremental, i.e., supports local reconstruction updates.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method for fast anatomical mapping reconstruction, the method comprising:
presenting, on a display, an electroanatomical (EA) map of a surface of a cavity of an organ;
receiving input from a user; and
in response to the user input, locking a region of the EA map to subsequent updates, wherein locking the region comprises preventing subsequent updates in prespecified proximity of an anatomical feature in the EA map and wherein the EP map comprise an EA map of the left atrium, and wherein the anatomical feature is a pulmonary vein.

2. The method according to claim 1, wherein locking the region comprises preventing subsequent manual editing of the EA map.

3. The method according to claim 1, wherein locking the region comprises ignoring subsequently acquired data points belonging to the region.

4. The method according to claim 1, wherein locking the region is performed in response to identifying that data points in the region were obtained by a probe while applying excessive force to the surface.

5. The method according to claim 1, and comprising manually editing unlocked regions of the EA map to remove irrelevant data points therein.

6. The method according to claim 1, and comprising:
unlocking the locked region;
manually editing the unlocked region of the EA map to remove irrelevant data points therein; and
re-locking the manually edited region.

7. A system for fast anatomical mapping reconstruction, the system comprising:
a display, which is configured to present an electroanatomical (EA) map of a surface of a cavity of an organ; and
a processor, which is configured to receive input from a user, and, in response to the user input, to lock a region of the EA map to subsequent updates, wherein the processor is configured to lock the region by preventing subsequent updates in prespecified proximity of an anatomical feature in the EA map and wherein the EP map comprise an EA map of the left atrium, and wherein the anatomical feature is a pulmonary vein.

8. The system according to claim 7, wherein the processor is configured to lock the region by preventing subsequent manual editing of the EA map.

9. The system according to claim 7, wherein the processor is configured to lock the region by ignoring subsequently acquired data points belonging to the region.

10. The system according to claim 7, wherein the processor is configured to lock the region in response to identifying that data points in the region were obtained by a probe while applying excessive force to the surface.

11. The system according to claim 7, wherein the processor is configured to receive further user input that manually edits unlocked regions of the EA map to remove irrelevant data points therein.

12. The system according to claim 7, wherein the processor is configured to:
unlock the locked region;
receive further user input that manually edits the unlocked region of the EA map to remove irrelevant data points therein; and
re-lock the manually edited region.

* * * * *